United States Patent
Bernard et al.

(10) Patent No.: US 10,106,765 B2
(45) Date of Patent: Oct. 23, 2018

(54) METHOD AND UNIT FOR PRODUCING MICROALGAE

(71) Applicants: Inria Institut National De Recherche En Informatique Et En Automatique, Le Chesnay (FR); Centre National De La Recherche Scientifique (C.N.R.S), Paris (FR); Ecole Centrale Paris, Chatenay Malabry (FR); Universite Pierre Et Marie Curie (Paris 6), Paris (FR)

(72) Inventors: Olivier Bernard, Carros (FR); Filipa Lopes, Paris (FR); Eric Pruvost, Nice (FR); Antoine Sciandra, Villefranche sur mer (FR)

(73) Assignees: Inria Institut National De Recherche En Informatique Et En Automatique, Le Chesney (FR); Centre National De La Recherche Scientifique (C.N.R.S), Paris (FR); Ecole Centrale Paris, Chatenay Malabry (FR); Universite Pierre Et Marie Curie (Paris 6), Paris (FR)

( * ) Notice: Subject to any disclaimer, the term of this patent is extended or adjusted under 35 U.S.C. 154(b) by 301 days.

(21) Appl. No.: 14/905,469

(22) PCT Filed: Jul. 15, 2014

(86) PCT No.: PCT/EP2014/065126
§ 371 (c)(1),
(2) Date: Jan. 15, 2016

(87) PCT Pub. No.: WO2015/007724
PCT Pub. Date: Jan. 22, 2015

(65) Prior Publication Data
US 2016/0152933 A1 Jun. 2, 2016

(30) Foreign Application Priority Data

Jul. 15, 2013 (FR) ..................................... 13 56955

(51) Int. Cl.
*C12M 1/00* (2006.01)
*C12M 1/12* (2006.01)
(Continued)

(52) U.S. Cl.
CPC ............ *C12M 21/02* (2013.01); *C12M 23/48* (2013.01); *C12M 25/02* (2013.01); *C12M 33/18* (2013.01);
(Continued)

(58) Field of Classification Search
CPC ..................................................... C12M 21/02
See application file for complete search history.

(56) References Cited

U.S. PATENT DOCUMENTS

2010/0144017 A1    6/2010    Shepherd

FOREIGN PATENT DOCUMENTS

WO    2012/171123 A1    12/2012
WO    2013/071364 A1    5/2013

*Primary Examiner* — Rosanne Kosson
(74) *Attorney, Agent, or Firm* — Maynard Cooper & Gale, P.C.; Brian T. Sattizahn

(57) ABSTRACT

The invention relates to a method for producing microalgae on a support (14) that is movably mounted essentially in an aqueous medium contained in a tank (12), said method comprising a succession of phases in which the microalgae developing on the support (14) are exposed to sunlight and phases in the shade, the light intensity received in the shade being less than 50% of the average light intensity received during the sunlight exposure phases. The total length of the shade phases is more than 50% longer than the total length of the sunlight exposure phases.

5 Claims, 4 Drawing Sheets

(51) Int. Cl.
*C12M 1/26* (2006.01)
*C12M 3/00* (2006.01)
*C12N 1/12* (2006.01)
(52) U.S. Cl.
CPC ............ *C12M 33/20* (2013.01); *C12M 41/08* (2013.01); *C12N 1/12* (2013.01)

METHOD AND UNIT FOR PRODUCING MICROALGAE

The present invention relates to a method for producing microalgae on a support movably mounted essentially in an aqueous medium contained in a tank comprising successive phases of exposing the microalgae growing on the support to sunlight and phases of said microalgae residing in the shade, the light intensity received in the shade being less than 50% of the average light intensity received during the phases of exposure to sunlight.

The production in aqueous medium of microalgae or any other photosynthetic microorganism is used to meet the needs of the cosmetics markets, the pharmaceutical industry, aquaculture, the production of functional food or food supplements, and also the production of bioenergy, by utilizing the ability of microalgae to capture light energy to fix inorganic carbon (mainly in the form of carbon dioxide or bicarbonate).

Microalgae are most commonly cultured in suspension in a liquid medium, the surface of which is exposed to the sun. To ensure that each cell can be at least intermittently exposed to the light, the medium is stirred, for example by means of paddle wheels. There are also closed bioreactors, composed of a transparent chamber equipped with a stirring device or means for causing the liquid stream to circulate between two walls, enabling exposure to a light source.

Irrespective of their nature, these units, which require the movement of the culture medium, are highly energy-consuming. Moreover, harvesting the microalgae itself requires a large amount of energy, due to the low concentration thereof and the small difference in their density compared to that of the medium, thereby making their separation tricky. This separation is commonly carried out by centrifugation which is also energy-consuming.

Microalgae may also grow on a mobile support such as a closed-loop support, circulating on rollers which are completely or partially immersed in an aqueous medium.

Such a unit, which aims to maximize the exposure of the microalgal biofilm at the surface of the support to an artificial or natural light source so as to optimize the growth thereof, is described for example in document AU 2012 101 593. The microalgae are exposed to light essentially when the portion of the support on which they accumulate is above the surface. Combining natural light sources and artificial light sources (light-emitting diodes) makes it possible to maximize the light intensity, especially during variations in the light intensity of the sun, as indicated in paragraph [0063].

Even though these methods enable an easier harvest which is less energy-consuming compared to the processes for producing microalgae in suspension, their yields remain modest, especially in strong light.

The aim of the invention is to propose a method for producing microalgae which improves the yield, especially in high light intensities.

To this end, a subject of the invention is a method for producing microalgae, characterized in that the total duration of the phases of residing in the shade is 50% greater than the total duration of the phases of exposure to sunlight.

According to particular embodiments, the invention comprises one or more of the following characteristics:
the total duration of the phases of residing in the shade is between 2 and 10 times the total duration of the phases of exposure to light;
the duration of each phase of exposure to light is between 5 seconds and 10 minutes;
the support circulates in a loop between rollers, and the speed of the support is between 1 cm/s and 1 m/s;
the total dose of illumination of the microalgae during each exposure phase is between 1 and 60 millimol photons/m$^2$;
the microalgae are part of one or more of the species from the group consisting of *Botryoccocus* sp., *Porhyridium* sp., *Cylindrotheca* sp., *Navicula* sp., *Haslea* sp. and *Chlorella* sp.; and
the microalgae are kept in the aqueous medium at least 90% of the time.

The invention also relates to a unit for producing microalgae comprising one or more of the following characteristics:
said unit for producing microalgae comprises:
a tank;
a support movably mounted in an aqueous medium contained in the tank; and
means for driving and guiding the support successively over sections for exposing the microalgae on the support to sunlight and over sections for resting in the shade, the arrangement being such that the light intensity received during travel on the sections for resting in the shade is less than 50% of the average light intensity received during travel on the sections for exposure to sunlight, characterized in that the means for driving and guiding the support are set up such that the total duration of travel on the sections for resting in the shade is 50% greater than the total duration of travel on the sections for exposure to sunlight.
the support is folded into a loop and the support is guided along superposed sections, the upper section forming an exposure section arranged above the other sections forming rest sections located in the shadow of the exposure section;
the support is folded into a loop and comprises means for guiding the support along vertical rising and falling sections substantially perpendicular to the surface of the aqueous medium which is contained in the tanks which are arranged in the shade; and
the support is a Möbius strip.

The invention will be better understood upon reading the following description, given solely by way of example and with reference to the drawings, in which.

Irrespective of the embodiment, the invention described below is particularly suited to zones subjected to high light intensities produced by solar radiation. Within the meaning of the present patent application, high light intensities are greater than 300 micromol photons/$m^2$/s.

Figure 1:
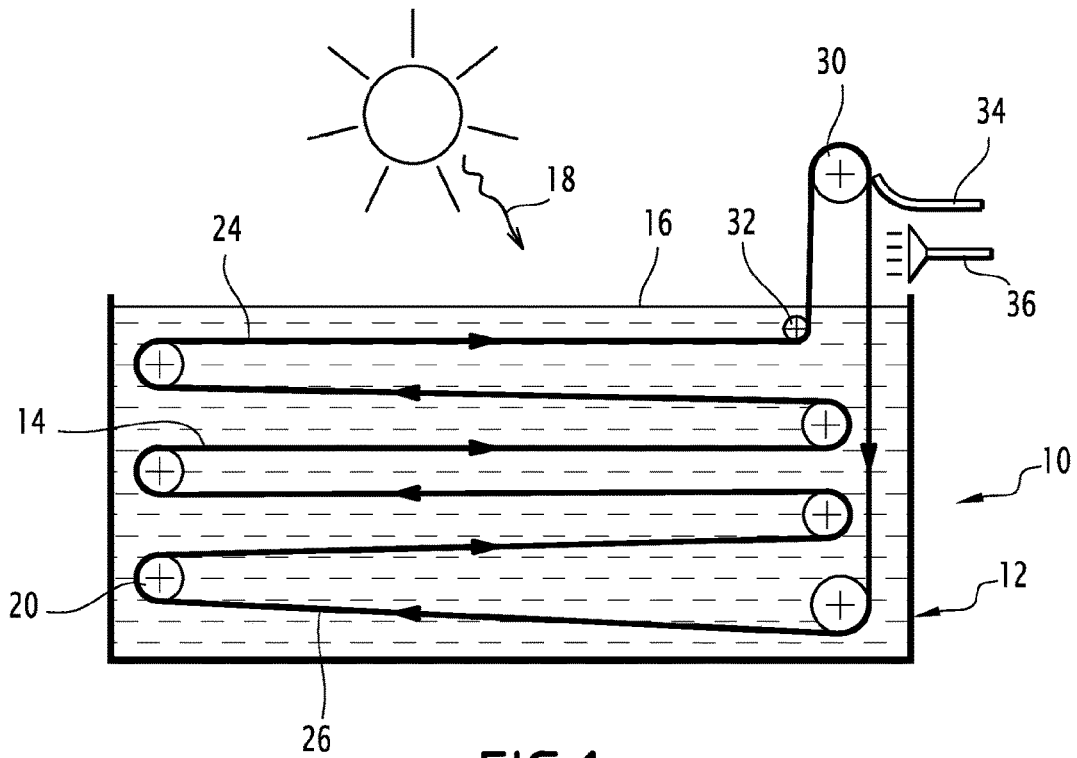
FIG. 1 is a diagrammatic side view of a unit for producing microalgae according to the invention.

The unit 10 shown in FIG. 1 essentially comprises a tank 12 and a support 14 circulating in the tank 12 and on which microalgae grow, forming a biofilm.

The microalgae are cells of between 1 and 100 micrometers in size. These microalgae are part of one or more of the species *Botryoccocus braunii, Porhyridium cruentum*, and epipelic species such as *Cylindrotheca closterium* or *Navicula salinarum*. Species cultured in this way, alone or in conjunction with other algae such as *Chlorella sorokiniana* and/or bacteria, are advantageously used to break down or fix elements in water.

The tank 12 is open at its upper part. The surface thereof, denoted 16, is directly exposed to solar radiation 18 and extends over the whole open surface of the tank 12. It has an area of between 0.1 $m^2$ and 10 000 $m^2$ and preferably of between 10 and 1000 $m^2$. The unit does not have any light source for exposing the microalgae, other than the sun.

The tank 12 consists, for example, of a brick-built vessel, or else a natural body of water such as a lake or pond, or even a bay. As a variant, the tank is a water treatment tank of a purification plant, especially one suited to treating inorganic nitrogen and phosphorus.

Preferably, the water contained in the tank is continually renewed.

When it is a brick-built vessel, the tank is between 10 cm and 150 cm deep, and preferably between 50 cm and 1 m deep. Preferably, it is deeper than 50 cm.

The support 14 is formed from a strip closed onto itself in a loop and guided by a set of turning and guiding rollers 20. At least one of the rollers is motorized to drive the support 14.

The support is formed, for example, from a belt to provide mechanical strength, which is covered on one face with a woven polymer sheet or any other flexible support. The support for the biofilm is preferably a rough, hydrophobic support with cavities or microcavities. It has sufficient flexibility to withstand passage over the rollers. It is resistant to light, and in particular to ultraviolet rays. The material is chosen such that any deterioration thereof does not affect the biological activity.

Materials such as cotton, hessian, polyethylene and polyurethane are suitable as biofilm support sheet. Polyester and polyurethane sheets used in food processing and colonized by bacteria are especially suited.

Advantageously, biopolymers are used to form the biofilm support sheet.

The support is advantageously between 0.1 m and 2 m wide. The total length thereof is for example between 1 m and 5000 m.

The ratio between the volume of liquid medium contained in the tank 12, the open surface area 16 and the surface area of the support is determined so as to avoid too great a heating of the tank under the effect of solar radiation, such that the temperature of the medium remains between 20° C. and 35° C.

In the embodiment of FIG. 1, two vertical rows of rollers are arranged at the two opposite ends of the tank 12.

The rollers are arranged with their axes parallel to the surface of the water 16. The axes of the rollers are parallel to one another. The rollers are arranged one above the other on either side of the tank such that the support circulates on sections which are generally horizontal from one roller to another roller on the opposite side, the support being turned on each roller.

The arrangement is such that the support circulates along sections which are superposed and parallel to one another and to the surface of the water 16. Thus, the support circulates along a boustrophedon path. The section for circulating the support which is arranged immediately below the surface 16 forms a section 24 for exposing the microalgae to solar radiation through the surface 16.

The exposure section 24 is located at a depth of between 3 cm and 20 cm from the surface 16. The depth is advantageously chosen such that the support is as close as possible to the surface 16 while limiting interactions with surface ripples. The light intensity on the exposure section 24 is then advantageously between 100 and 400 micromol photons/$m^2$/s.

On its exposure section 24, the support covers the other sections for circulating the support which are arranged at a lower level. These lower circulation sections, forming rest sections 26, are masked from direct solar radiation by the presence of the exposure section 24 which is generally opaque, and are thus located in the shade.

Within the meaning of the patent, shade constitutes a part of the medium in which the light intensity resulting from sunlight is reduced to a value which is less than 50% of the average light intensity received on the exposure section 24.

Thus, the light intensity in the shade, to which the microalgae on the rest sections 26 are exposed, is less than 100 micromol photons/$m^2$/s and preferably less than 10 micromol photons/$m^2$/s. In the embodiment shown, there are five rest sections 26, along which the support is in the shade. The support advantageously circulates from the bottom of the tank 12 to the upper surface 16 along the various rest sections 26, before travelling across the exposure section 24.

The speed of circulation of the support is preferably between 1 cm/s and 1 m/s. The speed is advantageously adapted to the direct sunlight received by the section 24, such that the dose of illumination received by the biofilm during each passage over an exposure section 24 does not exceed 60 millimol photons/$m^2$. Thus, the passage time over the exposure section 24 is less than 10 minutes and generally between 1 and 3 minutes.

The exposure section 24 is between 0.1 m and 1000 m long. The length and speed thereof are such that the duration of the phases of exposing the microalgae to direct sunlight, that is to say the duration of circulation of the microalgae on the exposure section 24, is between 5 s and 10 min depending on the light intensity at the surface.

It is understood that, in the illustrated example, the microalgae reside in a zone of shade during circulation on the rest sections 26 for a total duration around five times greater than the total duration of exposure to light during circulation on section 24.

Preferably and more generally, according to the invention, the total duration of the phases of residence in a zone of shade is fifty percent (50%) greater than the total duration of the phases of exposure to light.

Advantageously, especially for high sunlight intensities above 1000 micromol/$m^2$/s, the total duration of the phases of residence in a zone of shade is between 2 and 10 times the total duration of the phases of exposure to light. It is preferably at least 5 times greater than the total duration of the phases of exposure to light.

In addition, preferably, the total duration of the phases of residence in a zone of shade is at most 10 times greater than the total duration of the phases of exposure to light.

Finally, preferably, the value of the average light intensity received by a microalga passing through successive exposure and shade phases is less than a threshold, for example of 100 micromol photons/m²/s, during the sunlit periods of the unit, that is to say during the day. This average value corresponds to the average value received by a microalga over a cycle, during sunlit periods of the unit. The term "cycle" is intended to mean the passage of a biofilm such as a microalga over all the rest sections 26 and over the exposure section 24 such that the biofilm passes only once over each of the sections 24, 26 in question.

The unit also comprises a roller 30 arranged above the surface 16 of the tank. The support circulates on this roller 30 after having moved onto a roller 32 forming a right-angle gear arranged at the final end of the exposure section 24. A moveable scraper 34 is mounted facing the roller 30 in order to scrape the support and to take off the surface microalgae, during the harvest phases.

The scraper is put in place at time intervals making it possible to keep the thickness of the biofilm around a predefined average value such that the degree of respiration in the biofilm layer in contact with the support is substantially equal to the degree of inorganic carbon fixation through photosynthesis of this same contact layer, such that the amount of carbon fixed in the contact layer of the biofilm is between half and double the amount of carbon lost by respiration of the microorganisms of the biofilm. Ideally, the harvest is carried out once a day to once a week, so as to keep the thickness of the biofilm around this value.

In addition, the unit comprises a sprayer 36 for spraying nutritive elements which form sources of nitrogen, of phosphorus, of vitamins and of micronutrients on the section for returning the support 14 into the tank 12.

The time spent outside the culture medium makes it possible to degas the oxygen accumulated in or near the biofilm, and to enrich the biofilm in carbon dioxide.

It is observed that the unit described here, and also the method for producing microalgae that the unit employs, make it possible to avoid too great a heating of the biofilm and to obtain high photosynthetic efficiency, because, since the microalgae are only exposed directly to solar radiation for a moderate period of time, they are not subjected to photoinhibition.

In a variant, the unit comprises means for adjusting the ratio between the total exposure time and the total residence time of the biofilm in the shade, especially to take account of the light intensity provided by the sun. These means comprise for example means for moving, parallel to the surface 16, a roller at the end 20 of the exposure section 24. The movement of the roller ensures lengthening or shortening of the exposure section, consequently increasing or decreasing the abovementioned ratio.

To ensure tension of the support, another roller at the end of the rest section 26 is jointly moveable to correspondingly adapt the length of the return section.

In yet another variant, the unit comprises means for adjusting the speed of circulation of the support to increase or decrease the exposure time.

According to a particular embodiment, the tank comprises means for adjusting the height of water in the tank in order to keep the temperature in a range of predetermined values.

Figure 2:
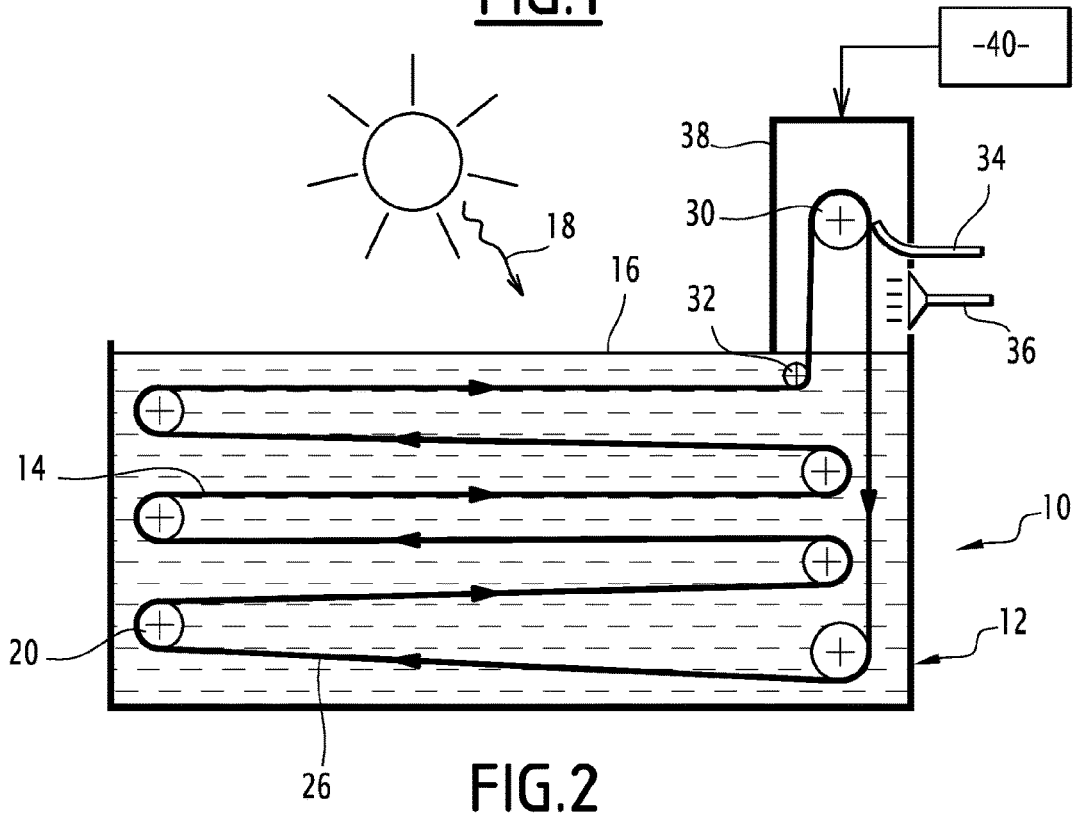
FIG. 2 is an identical view to that of FIG. 1, of a variant embodiment.

In the variant embodiment illustrated in FIG. 2, the unit comprises, in addition to the elements provided in FIG. 1, a chamber 38 for injecting carbon dioxide. The chamber 38 hermetically covers the section of the support which emerges above the surface 16 of the tank. This chamber opens into the tank, below the surface 16, thereby delimiting a confined space filled with an atmosphere which is richer in carbon dioxide than the air. The interior of the chamber 38 is connected to a source 40 for injecting carbon dioxide so as to ensure an atmosphere rich in carbon dioxide therein. Preferably, the content of carbon dioxide in the chamber is greater than 3% as volume ratio.

It is understood that, during the circulation of the support inside the chamber 38, the microalgae borne by the support are brought into contact with carbon dioxide, thereby enabling the capture thereof under the action of the solar radiation to which they have been exposed beforehand.

In the following embodiments, a harvesting section not shown, such as that described with regard to FIG. 1, is used. Advantageously, the roller 30 is moveably mounted and is kept under the level of the surface 16 in the aqueous medium except for during the harvesting phases and emerges only during the harvesting phases.

Figure 3:
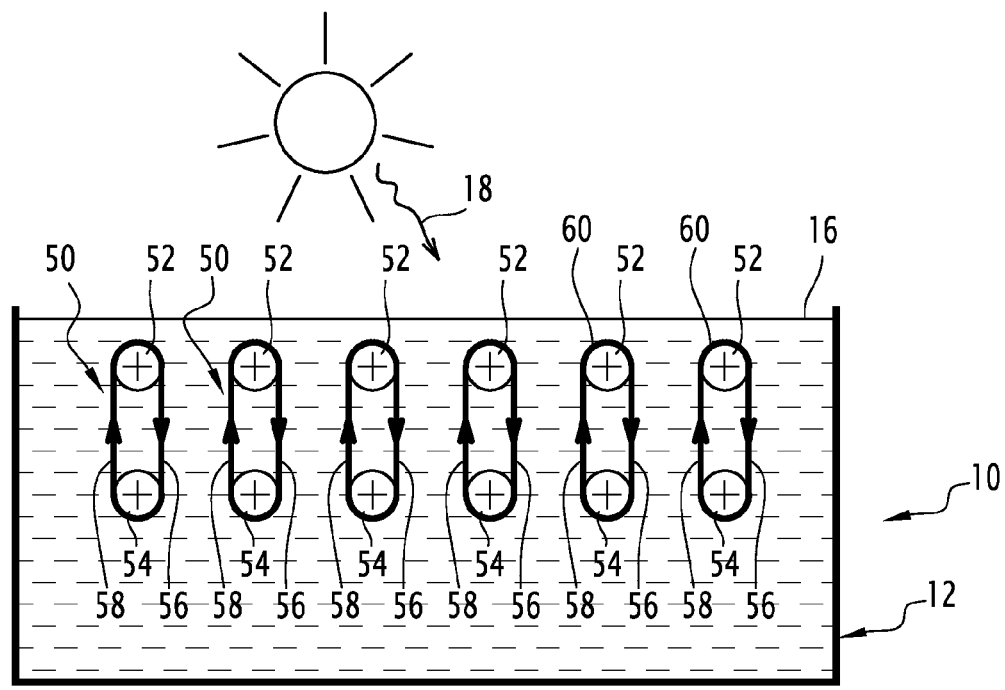
FIG. 3 is a simplified schematic side view of another embodiment of a unit for producing microalgae according to the invention.

In the embodiment of FIG. 3, the tank 12 contains several closed-loop supports 50 arranged parallel to one another. These independent supports 50 are only wrapped around two turning rollers arranged one above the other. One of the rollers is motorized to drive the support. An upper turning roller 52 is arranged immediately below the surface 16 whereas a lower turning roller 54 is arranged deeper, in line with the roller 52.

The strip forming the support thus circulates essentially vertically between the two rollers, along a falling side 56 and a rising side 58. In this embodiment, the microalgae borne by the exposed surface of the support are subjected to phases of exposure to sunlight on an exposure section denoted 60 only on the upper half-perimeter of the upper roller 52 while the support is turning. During the falling 56 and rising 58 sections, and during the turning about the lower roller 54, the support is kept in the shade, with any exposure to sunlight giving rise to a weak light intensity given the incidence of the solar radiation in relation to the support and given the greater depth at which the support is located.

Figure 4:
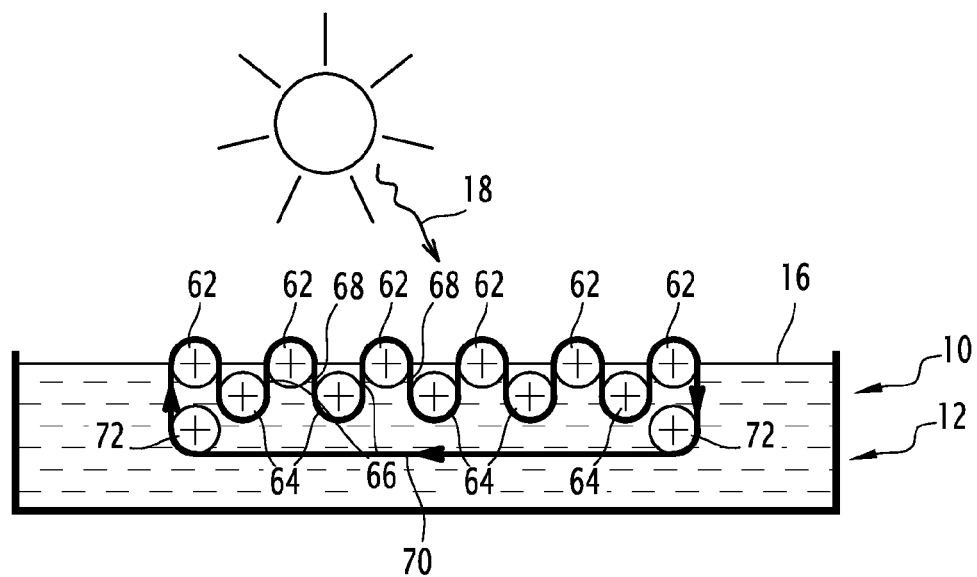
FIG. 4 is an identical view to that of FIG. 3, of a variant embodiment.

In the variant embodiment illustrated in FIG. 4, a single support is arranged between two series of upper 62 and lower 64 rollers to form successive rising 66 and falling 68 sections. Thus, as in the embodiment in FIG. 1, the support circulates along a boustrophedon path but with straight, vertical circulation sections, completed by a return path 70 between two extreme lower rollers 72. Thus, the return section 72 is below the lower rollers 64.

In this variant embodiment, the axis of the rollers 62 extends substantially in the plane of the surface 16 of the tank such that the upper half of the rollers 62 is located outside the aqueous medium, and is directly subjected to solar radiation, while the lower half of the rollers 62 is kept in the liquid medium. As above, the strip is only subjected to exposure to sunlight on the upper half of the rollers 62 constituting the exposure section denoted 74, the strip circulating in the shade for the remainder of its path.

Figure 5:
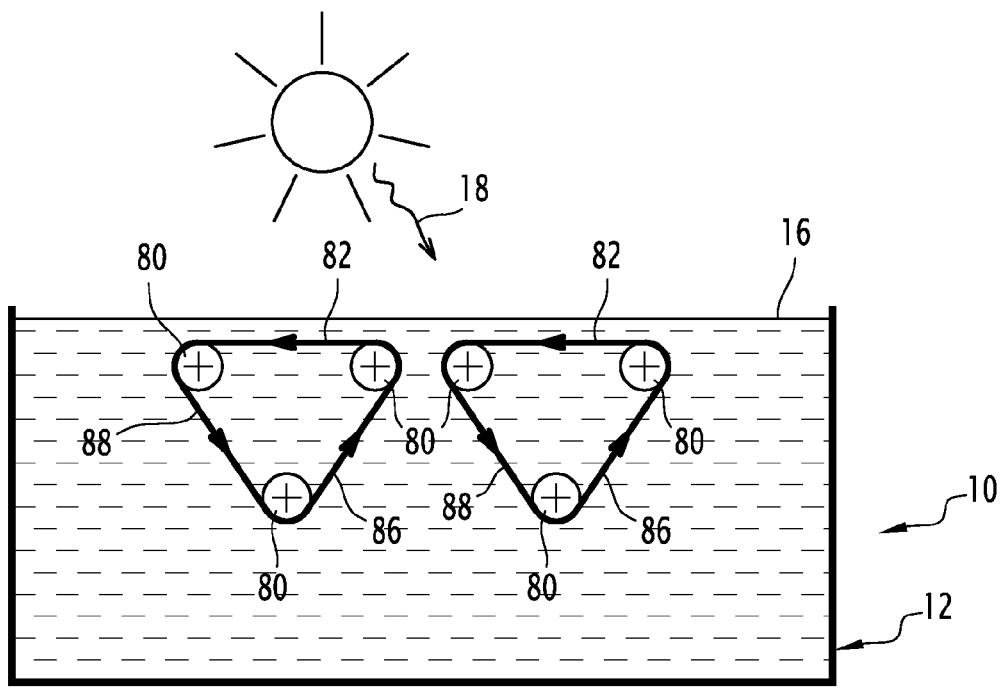
FIG. 5 is a simplified schematic side view of yet another embodiment of a unit for producing microalgae according to the invention.

In the embodiment in FIG. 5, each strip is guided by three rollers 80 delimiting circulation sections extending along the three sides of an equilateral triangle. One of the sides of the triangle defining the exposure section, denoted 82, extends parallel to the surface 16 of the tank, with the two other sides which form rising 86 and falling 88 rest sections extending under the exposure section 82, in the shadow thereof.

In this embodiment, the total time of circulation in a zone of shade is double the total duration of exposure.

Figure 6:
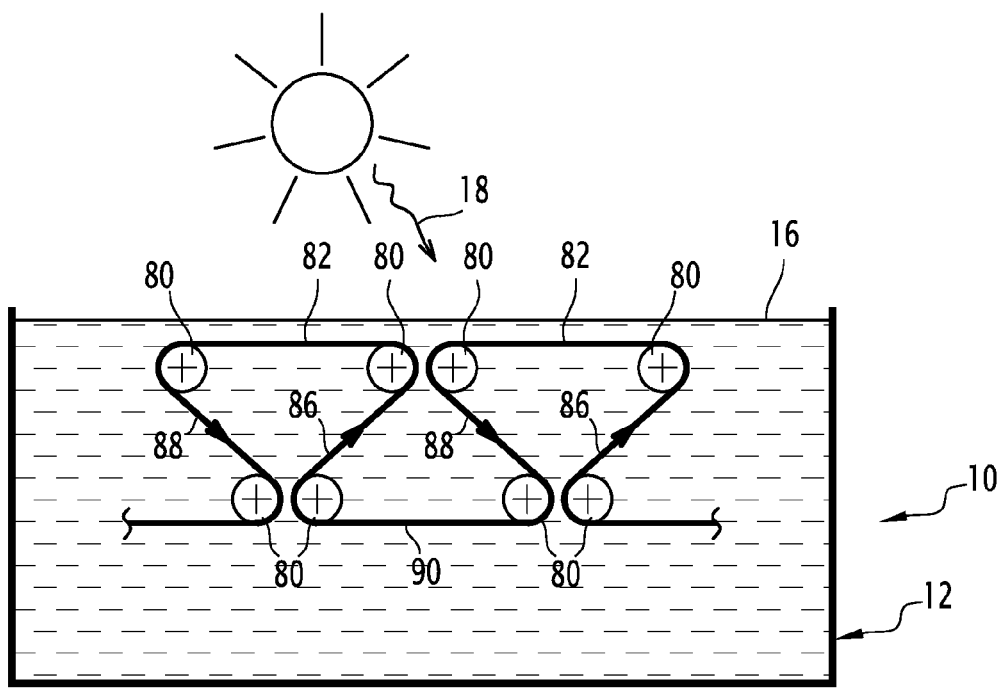
FIG. 6 is an identical view to that of FIG. 5, of a variant embodiment.

In the variant embodiment in FIG. 6, the lower rollers have been replaced by rollers enabling the circulation of the same strip successively over the various exposed sections 82 after circulation on the two falling 88 and rising 86 sections, these two sections being connected by a lower connecting section 90, also arranged in the shade. A return section arranged at depth (not shown) ensures the return of the strip from one end to the other of the tank.

In this embodiment, the total circulation time in a zone of shade is more than triple the total duration of exposure.

Figure 7:
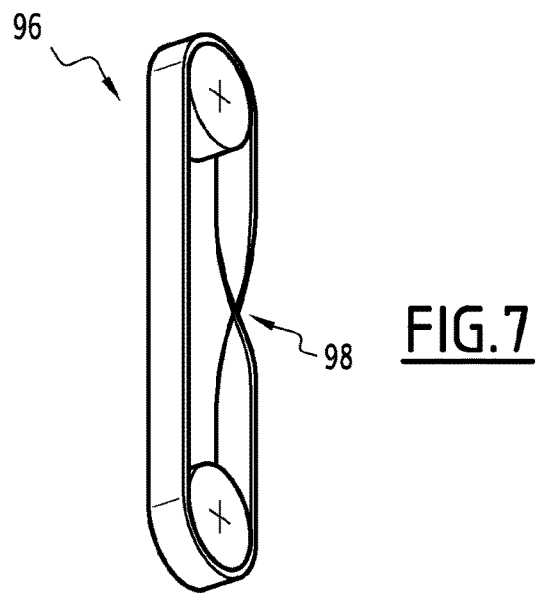
FIG. 7 is a simplified schematic side view of a final embodiment of a unit for producing microalgae according to the invention.

In each of the embodiments described above, the microalgae grow mainly on a single face of the support. As a variant, which is applicable to all the embodiments, the support which comprises a biofilm on both its faces is formed of a Möbius strip 96, such that the closed-loop support comprises a single face due to the strip turning about its circulation axis in a section 98 as illustrated in FIG. 7. Thus, microalgal growth occurs over the whole of the surface of the support, with the support having a different orientation during each passage over the exposure section(s). Advantageously, the section for turning the strip is on a rest section, allowing complete exposure of the support over the exposure section(s).

For each of the above embodiments, as a variant, the unit comprises means for injecting nutrients and/or carbon dioxide into the aqueous medium, enabling the medium to be enriched in nutrients and/or carbon dioxide during the circulation of the support and the growth of the biofilm.

As a variant, the invention not only employs a photosynthetic mechanism for growing the biofilm, but also employs a mechanism for consuming organic carbon, especially sugars and organic acids present in the aqueous medium. The method then employs mixotrophy.

As a variant, irrespective of the embodiment, the tank is covered by a transparent greenhouse, allowing the circulation of air and preventing contamination of the aqueous medium.

Figure 8:
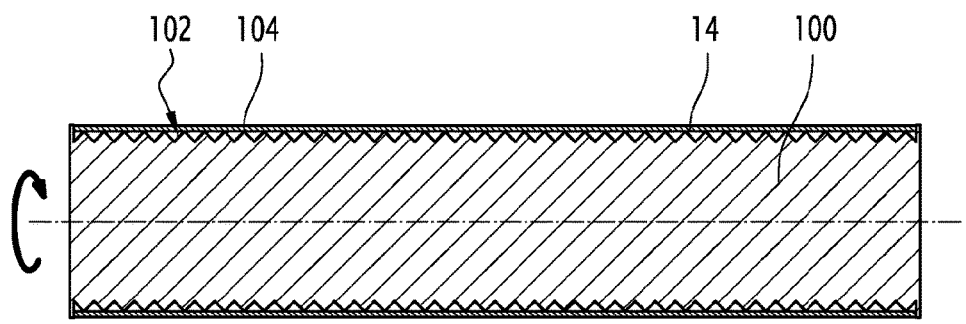
FIG. 8 is a view in longitudinal section of an exemplary embodiment of a roller from a unit from the previous figures.

FIG. 8 illustrates an example of a roller 100 for turning the circulating support 14 in the form of a strip. In order to reduce the surface area of contact between the biofilm and the roller 100, the external surface of the roller comprises an external profile with projections and recesses formed for example of a contacting helical profile 102 extending along the whole, generally cylindrical, surface of the roller. As a variant, the surface is provided with adjoining grooves parallel to one another, each groove being arranged transversely to the axis of the roller.

It is appreciated that, with such a profile, the biofilm, when it is in contact with the external surface of the roller 100, only makes contact along isolated contact lines denoted 104, thereby reducing any deterioration of the biofilm by the roller.

Figure 9:
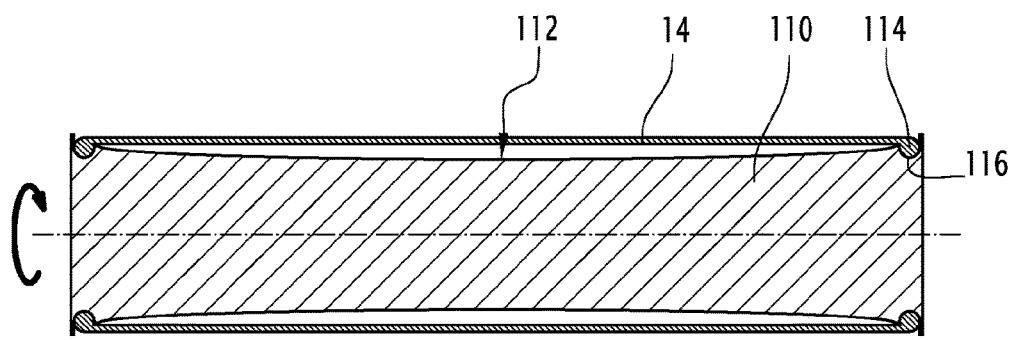
FIG. 9 is an identical view to that of FIG. 8, of a variant embodiment.

In the alternative embodiment illustrated in FIG. 9, the roller denoted 110 has a concave external surface 112 such that the diameter of the roller gradually increases from its median part to its opposite ends. The support 14 in the form of a strip comprises laterally, along its whole length, longitudinal beads 114 on either side received in annular grooves 116 made at the two ends of the roller 110. In these conditions, the median part of the strip 114 is kept taut between the two beads 116 held in the grooves 114.

Due to the recessed shape of the lateral surface of the roller 110, the main extent of the support 14 stays held away from the surface of the roller, thereby avoiding any risk of deterioration of the biofilm formed on the surface of the support facing the roller.

The invention claimed is:

1. A method for producing microalgae on a support movably mounted in an aqueous medium contained in a tank comprising:

successive phases of exposing the microalgae growing on the support to (a) sunlight and (b) shade, the light intensity received in the shade being less than 50% of the average light intensity received during the phases in the sunlight, characterized in that the total duration of the phases in the shade is 50% greater than the total duration of the phases in the sunlight, wherein the duration of each phase of exposure to sunlight is between 5 seconds and 10 minutes and the total dose of illumination of the microalgae during each exposure phase is between 1 and 60 millimol photons/m.

2. The method for producing microalgae as claimed in claim 1, characterized in that the total duration of the phases in the shade is between 2 and 10 times the total duration of the phases in the sunlight.

3. The method for producing microalgae as claimed in claim 1, characterized in that the support circulates in a loop around rollers, wherein the speed at which the support moves is between 1 cm/s and 1 m/s.

4. The method for producing microalgae as claimed in claim 1, characterized in that the microalgae are in one or more of the genera selected from the group consisting of *Botryoccocus, Porhyridium, Cylindrotheca, Navicula, Haslea* and *Chlorella*.

5. The method for producing microalgae as claimed in claim 1, characterized in that the microalgae are kept in the aqueous medium at least 90% of the time.

* * * * *